United States Patent [19]

Sato et al.

[11] Patent Number: 5,595,899
[45] Date of Patent: Jan. 21, 1997

[54] METHODS OF INTRODUCING FOREIGN DNA INTO CELLS

[75] Inventors: Masahiro Sato; Nobuhiro Tada, both of Kawagoe, Japan

[73] Assignee: Hoechst Japan Limited, Tokyo, Japan

[21] Appl. No.: 364,076

[22] Filed: Dec. 23, 1994

Related U.S. Application Data

[63] Continuation of Ser. No. 30,085, filed as PCT/JP91/01269, Sep. 24, 1991, abandoned.

[30] Foreign Application Priority Data

Sep. 25, 1990 [JP] Japan ..................................... 2-251843

[51] Int. Cl.$^6$ ........................... C12N 15/90; C12N 15/79; C12N 15/87; C07H 21/04
[52] U.S. Cl. ..................... 435/172.3; 435/69.1; 435/70.1; 435/70.3; 435/240.2; 435/252.3; 536/23.1; 935/34; 935/52; 935/70
[58] Field of Search ............................... 435/69.1, 240.2, 435/172.3, 252.3, 70.1, 70.3; 536/23.1; 935/52, 70, 34

[56] References Cited

FOREIGN PATENT DOCUMENTS

| 2144542 | 3/1985 | United Kingdom | G01N 1/30 |
| WO81/02426 | 9/1981 | WIPO | C12N 15/00 |
| WO88/05077 | 7/1988 | WIPO | C12N 15/00 |

OTHER PUBLICATIONS

Cotten et al. "Transferrin–Polycation Mediated Introduction of DNA Into Human Leukemic Cells . . . " Proc. Natl. Acad Sci. 87: 4033–4037 1990.
McNeil et al. "Glass Beads Load Macromolecules Into Living Cells" J. Cell Science 88:669–678 1987.
Zimmer et al. "Non–Intercalating DNA–Binding Ligands: Specificity of The Interaction & Their Use as Tools . . . " Biophys Molec. Biol. 47(1) 31–112 1986.
A Mammalian Cell Mutant With Enhanced Capacity to Dissociate a Bis–Benzimidazole Dye–DNA Complex, P. J. Smith et al., Carcinogenesis, 9(3):485–490 (1988).
Wagner et al., "Transferrin–polycation conjugates as carriers for DNA uptake into cells", Proc. Natl. Acad. Sci. USA 87:3410–3414 (1990).
Brackett et al., "Uptake of Heterologous Genome by Mammalian Spermatozoa and Its Transfer to Ova through Fertilization", Proc. Natl. Acad. Sci. 68:353–357 (1971).
Hahn et al., "Elimination of Plasmidic Determinants by DNA–complexing Compounds", Top. Infect. Dis.–Drug Recept. Interact. Antimicrob. Chemother. Symp. 1:99–113 (1974).
Lavitrano et al., "Sperm Cells as Vectors for Introducing Foreign DNA into Eggs: Genetic Transformation of Mice", Cell 57:717–723 (1989).

Primary Examiner—Mindy Fleisher
Assistant Examiner—Nancy J. Degen
Attorney, Agent, or Firm—Finnegan, Henderson, Farabow, Garrett & Dunner, L.L.P.

[57] ABSTRACT

The present invention provides an easy and efficient method of introducing a foreign DNA into certain cells which have been considered difficult to be transformed by conventional methods.

The present inventors have found that bis-benzimdazolyl compounds which specifically bind to DNA were useful as a carrier to introduce the DNA into a target cell. Foreign DNA was introduced into a host cell by exposing said cell to a suspension or a solution containing the foreign DNA-compound complex.

6 Claims, 1 Drawing Sheet

5,595,899

METHODS OF INTRODUCING FOREIGN DNA INTO CELLS

This application is a continuation, of application Ser. No. 08/030,085 filed as PCT/JP91/01269 Sep. 24, 1991, now abandoned.

FIELD OF THE INVENTION

The present invention relates to a method of introducing a foreign DNA into a cell using a compound capable of binding to a double-stranded DNA. Specifically, the invention relates to a method of obtaining a transformant, a cell transformed with a foreign DNA, by binding the foreign DNA to the compound to form a DNA:compound complex and then exposing a mammalian cell to a suspension or a solution containing the DNA:compound complex.

1. Prior Art

Numerous attempts have been made to express a foreign DNA in a host cell by introducing the DNA into the cell of higher organisms, especially animal cells. Indeed, various methods of obtaining a transformant, a cell containing a foreign DNA, have been proposed. For example, such methods include a calcium phosphate method (Graham, F. L. and Van Der Eb., A. J., 1973, Virology 52:456–467), a DEAE dextran method (Farber, F., et. al.,1975, Biochem. Biophys. Acta., 390:298–311; Pagano, J. S., 1970, Prog. Med. Virol. 12:1–48), a polyornithine method (Farber, F., et.al.,1975, Biochem. Biophys. Acta., 390:298–311), a DNA microinjection method (Cappechi, M. R., 1980, Cell. 22:479–488), a polyethylene glycol (PEG)/dimethylsulfoxide(DMSO) method (Jonak, Z. L., et.al., 1984, Hybridoma 3:107–118), a trypsin/EDTA/ glycerol (Chu, G. J. and Sharp, P. A., 1981, Gene 13:197–202), an osmotic shock method (Okada, G. Y., and Rechsteiner, M., 1982, Cell 29: 33–41), a liposome fusion method (Poste, G., et. al., 1976, Methods. Cell. Biol., 14:33–71; Fraley, R. et.al., 1980, J. Biol. Chem. 255; 10431–10435; Wong, T. K., et.al., 1980, Gene 10;87–94), a ghost red cell mediated method (Furusawa, M.,et.al., 1976, Methods. Cell. Biol.,14: 73–80; Straus, S. and Raskas, H., 1980, J. Gen. Virol. 48: 241–245; Godfrey, W., et.al., 1983, Proc. Natl. Acad. Sci. U.S.A. 80: 2267–2271 ), a bacterial protoplast fusion method (Chu, G. J. and Sharp, P. A., 1981, Gene 13:197–202; Sandri-Goldin, R. M., et.al., 1981, Mol. Cell. Biol. 1:743–752; Oi, V. T., and Morrison, S. L., 1986, Biotechniques 4: 214–221), a reconstituted Sendai virus envelope method (Loyter, A., et. al., 1984, Ciba. Found. Symp., 103:163–180), laser-beamporation (Tsuka koshi, M., et.al., 1984, Appl. Phys. B., 35: 2284–2289; Tao, W., et.al., 1987, Proc. Natl. Acad. Sci. U.S.A. 84: 4180–4184), a electroporation method (Neumann, E., et. al., 1982; EMBO. J., 1 :841–845; Potter, H., et.al., 1984, Proc. Natl. Acad. Sci. U.S.A. 81: 7161–7165), a tungsten microprojectile method (Klein, T. M., et. al., 1987, Nature 327: 70–73), a retrovirus vector method (Jaenisch, R., 1976, Proc. Natl. Acad. Sci. U.S.A., 73: 1260–1264: Jahner, D. and Jaenish, R., 1980, Nature 287:456–458). Each of these procedures is distinguished by its own spectrum of advantages and disadvantages with respect to efficiency, toxicity and specificity; a method used for a certain cell type may not always be used for the other.

A calcium phosphate method and a DEAE dextran method are suitable for phagocytic cells., e.g., fibroblast and L cell, while these methods are not suitable for poorly phagocytic cells, e.g., lymphocytes (Lewis, W. L., et. al., 1980, Somat. Cell. Genet. 6 :333–348).

These methods utilize an alteration of the cell membrane such as a temporary destruction of a part of the cell membrane and an increased permeability of the cell through a cellular modification or an endocytosis of the cell, except for the microinjection and the virus vector methods. The methods are based on the following mechanism: once a foreign DNA is introduced into a cell, some of the DNA enters the nuclear region of the cell by chance. Then, the DNA becomes incorporated into a host chromosome. However, transformation efficiency of such methods is fairly low (e.g., approximately $1/10^5$). In contrast, the microinjection method, in which a foreign DNA is directly introduced into the nucleus of the host cell via a micropipette, has a strikingly high transformation efficiency (e.g., approximately $1/10^3$ cell) as described by Cappechi, M. R.,1980, Cell 22:479–488. Although the microinjection method provides high transformation efficiency, the method requires high skills and special equipment and is not easily performed.

DISCLOSURE OF THE INVENTION

The present invention provides an easy and efficient method of introducing foreign DNA into certain cells which have been considered difficult to be transformed by conventional methods.

The present inventors have found that a certain compound specifically binds to DNA and successfully used the compound as a carrier to introduce the DNA into a target cell: We have introduced foreign DNA into a host cell by exposing the host cell to a suspension or a solution containing a foreign DNA:compound complex in which the compound is capable of binding to a double-stranded DNA. Specifically, foreign DNA is bound to the compound and a suspension or a solution containing the DNA:compound complex is added to a confluent cell culture (e.g., CHO cell line). The cell culture is then incubated for several hours under a selective condition. After incubation, we have found that a cell containing the foreign DNA (transformant) could be obtained.

The present invention provides a method of introducing a foreign DNA into a host cell by exposing the host cell to a suspension or a solution containing a DNA:compound complex.

There are two types of the binding of a compound to a foreign DNA. One of the types is termed an intercalative incorporation in which the whole molecule or the part of the molecule of the compound is inserted between stacked bases of DNA. Such compounds include actinomycin D, anthracycline compounds, and acridine compounds.

The other type is termed a non-intercalative incorporation in which the compound is not inserted between base pairs.

Any compound of the above types may be used as a carrier for a foreign DNA. The compounds of the non-intercalative type are preferable due to a lower probability to induce mutation in a host cell. Zimmer, C., et.al., (Prog.

Biophys. Molec. Bio., 47: 31–112, 1986) described compounds which bind non-intercalatively to DNA. The compounds of the non-intercalative type are classified into three groups: Compounds classified as antibiotics include netropsin (Finlay, A. C., et.al., 1951, J. Am. Chem. Soc. 73:341–343), distamycin A (Arcamone, F., et. al., 1958, German Pat. 1,027,667, Chem. Abstr., 1961, 55: 2012), mithramycin, chromomycin A3, olivomycin (Gause, G. F., 1967, In Antiobiotics, eds. D. Gottlieb and P. D. Shaw, p246–258), anthramycin (Horwitz, S. B., 1971, Prog. Molec. Subcell. Biol. 2:40–47), sibiromycin (Gause, G. H., 1975, In Antibiotics III eds. J. M. Corcoran and F. H. Hahn, p269–273), tomaymycin (Hurley, L. H., 1977, J. Antibiot., 30: 349–370), naphthyridinomycin (Kluepfel, D., et.al., 1975, J. Antibiot., 28: 497–502), saframycin A and C (Arai, T. et.al., 1977, J. Antibiot. 30: 1015–1018), and NSC-298223 (Hanka, L. J., et.al., 1978, J. Antibiot. 31:1211–1217).

Compounds classified as synthetic compounds include bis-benzimidazolyle compounds such as 2-[2-(4-hydroxyphenyl) benzimidazolyl-5]-5-(4-methylpiperazinyl-1)-benzimidazole [(hereafter referred to as Ho 33258), Loewe, H. and Urbanietz, J.,1974, Arzneim. Forsch. 24, 1927], 2-[2-(4-ethoxyphenyl) benzimidazolyl-5]-5-(4-methylpiperazinyl) benzimidazole [(hereafter referred to as Ho 33342), Arndt-Jovin, D. J., and Jovin, T. M., 1977, J. Histochem. Cytochem. 25: 585–589], berenil(Newton, B. A., 1967, Biochem. J. 105: 50–51), DDUG (4,4'-diacetyl-diphenylureabisquanylhydrazone) (Baguley, B. C., 1982, Molec. Cell. Biochem. 43: 167–181), ionenX (Day, R. A., et. al., 1978, Biochem. Biophys. Res. Commun. 84:969–977), mesotetra-(2-N-methylpyridyl)-porphine (Carvlin, M. J. and Fiel, R. J., 1983, Nucl. Acids. Res. 11: 6121–6138), DAPI (4,6-diamidino-2-phenylindole) (Mildner, B.,et.al., 1979, Cell. Molec. Biol 25: 399–407).

Compounds classified as steroid diamine compounds include irehdiamine A and malouetine (Silver, S., et. al., 1975, In antibiotics III eds. J. W. Corcoran and F. E. Hahn, p614–622).

The chemical structure of Ho 33258 and Ho 33342 is shown below.

Ho 33258 and Ho 33342 preferably bind to a double-stranded DNA and the DNA bound to the compound is visualized under UV illumination due to the generation of fluorescence. These properties of the compound have been used for staining the nuclei of viable cells (Zimmer, C. and Wahnert, U, 1986, Prog. Biophys. Molec. Biol.47: 31–112). The compound is barely toxic to cells and gives a clear image of the nuclear region microscopically, which property has been a great advantage for laboratory use. It is believed that Ho 33342 more readily penetrates through cell membranes than Ho 33258.

Although the above reagent has been used for staining cells and chromosomes, the reagent has never been used for introducing foreign DNA into a cell. The present inventor has focused on the properties of Ho 33342 and Ho 33258 capable of penetrating the cell membrane, localizing in the nuclear region and binding specifically to DNA and utilized the properties to introduce foreign DNA into a cell by exposing it to a solution containing the compound:DNA complex to the cell.

Target cells to be transformed include mammalian cells available from a cell culture collection such as CHO, NIH/3T3, L, LtK, FM3A (mouse mammary tumor), BHK (baby hamster kidney), CV-1, COS-1 (African Green Monkey kidney cell), HeLa (human uterocervical tumor cell), HL-60 (human promyelocytic leukemia), and human kidney derived 293, sperm cells and egg cells (at a pre-implantation stage), cells from fetus tissue, and protoplasts of plant cells.

Sperm cells and egg cells transformed according to the method of the invention will result in a transgenic animal and the method of the invention will open a novel way to produce a transgenic animal easily and efficiently. Sperm cells transformed with a foreign DNA are inseminated to egg cells, or egg cells transformed with a foreign DNA are allowed to develope into a fetus. Some of the newborns thus produced may possibly be a transgenic animal.

Ho 333258

Ho 33342

Certain cells readily take up the compound:DNA complex, but if a cell does not take up the complex, it is desirable to facilitate the uptake using the methods described below. The methods include a DEAE-dextran method, a calcium phosphate method, a polyomithine, a PEG/DMSO method, and a trypsine/EDTA/glycerol method. Alternatively, the physical method to assist the complex-uptake includes electroporation and a laser beam-poration. Furthermore, a toxic effect of the compound on cells can be minimized by concurrently using the reagent such as DiO-$C_5$-3 (3,3-dipentyloxacarbocyanine). Any double-stranded DNA can be used as a foreign DNA. It is preferable to use an expression vector DNA. Such foreign DNA includes a minimal expression unit consisting of a promoter, a gene of interest (a gene encoding a desired protein, e.g., cDNA) and a polyadenylation signal, or a genomic DNA containing a 5'-untranslated region, exon, intron, and 3'-untranslated region if desired. Cells are transformed with DNA, a mixture of the DNA and a selectable marker [e.g., neomycin resistant gene(neo), hygromycin B resistant gene(Hm')] or the DNA fused with the above selectable marker.

Suitable conditions of introducing a foreign DNA into a cell may be solely determined by transformation efficiency. These conditions that may influence transformation efficiency include a host cell type, a species of compounds, a concentration thereof, an incubation time, a form of DNA (e.g., circular or linear) and a concentration thereof.

A CHO (Chinese hamster ovary) cell, for example, is transformed at the time when it is subconfluent. The Ho 33342: DNA complex is added to the CHO cell culture and incubated for a couple of hours. A large amount of DNA and Ho33342 generally increases the transformation efficiency. However, when 12 uM or more of Ho 33342 is added to the cell culture and the culture is incubated over 20 hours, the growth of the CHO cell is inhibited. If a fairly high concentration of Ho33342 is used, the incubation time should be limited within 2–20 hours. Typically, a concentration of 0.2–6 uM Ho 33342 and 20 hours incubation may be preferable for transformation. Transformation efficiency is further increased by adding a fairly high concentration of Ho 33342 (e.g., 12 uM) to the cell in a serum-free medium and by incubating the culture in a short period of time (e.g., 2 hours). A suitable amount of DNA for transformation is 0.1–10 ug for a 60 mm culture plate. The form of DNA may be any form (e.g., circula, linear) and the size of DNA may be in the range from the molecular weight 2–3 kb to 30kb. One of the best candidates will be pSV2neo where additional DNA may be inserted. After transformation of the cell with the Ho 33342: DNA complex, the transformant is screened for the selective marker (e.g., antibiotic resistance gene like neo). In the present invention, the selectable marker already present in the foreign DNA is used.

BEST MODE TO PRACTICE THE INVENTION

Figure 1:
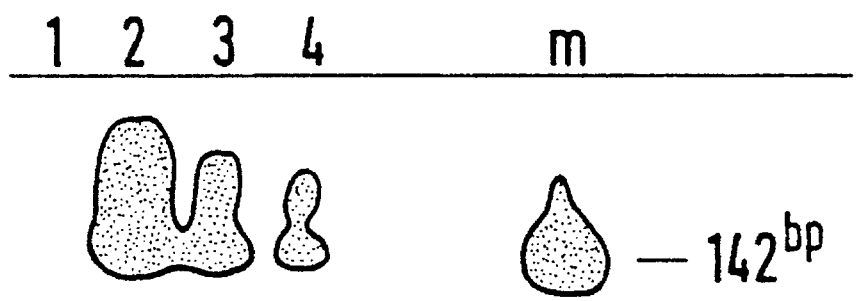
FIG. 1 shows a Southern blot hybridization after electrophoresis of chromosomal DNA amplified by the PCR. M;a positive control (0.2 ug of pSV2 neo), lane 1; the DNA of the CHO-dhfr⁻ cell before transformation, lane2–4; the DNA of the CHO-dhfr⁻ cell transformed with the Ho 33342(12.5 uM): DNA complex.

The present invention will be described in detail in the following Methods and Examples. The examples are intended to illustrate the invention and do not limit the scope of the invention.

Chromosomal DNA is isolated and purified from the G-418 resistant cell culture.
Isolation and Purification of Chromosomal DNA from G-418 Resistant Transformant Culture A G-418 resistant colony was aspirated using a microcapillary tube and transferred to a 24-well plate (Falcon; No. 3047) containing 1 ml of a culture medium [MEM-α+- Gibco; No. 410–1900), 10% fetal calf serum (Gibco), 400 ug/ml of G-418 (Gibco; No. 860–1811)] per well. The plate was incubated at 37° C., under 5% $CO_2$/95% air atmosphere for 10 days. 0.5 ml of trypsine solution (o.o25% trypsine, 0.02% EDTA(w/v) in phosphate buffer) was added to each well and the plate was incubated at 37° C. for 5 minutes. The cell was harvested by centrifugation (1300 r.p.m., for 3 minutes, at room temperature). 500 ul of lysis buffer (6 mg/ml of proteinase K and 20 mg/ml of proteinase E was dissolved in a solution containing 50mM Tris-HCl/pH8.0, 0.1M NaCl, 20mM EDTA and 1% SDS) was added to the cell. The lysate was incubated with shaking at 37° C. for 24 hours. 500 ul of phenol equilibrated with TE (10mM Tris-HCl , 1 mM EDTA, pH8.0) was added to the lysate and the mixture was incubated with shaking at room temperature for 30 minutes. The mixture was then centrifuged at 15,000 rpm for 10 minutes at 4° C. and the supernatant was saved. The extraction was repeated two more times. 10 ul of RNase A [(4 mg/ml);(Sigma)], which was dissolved in 0.15M NaCl, was added to the supernatant. The mixture was vortexed and incubated at 37° C. for more than 3 hours. After the RNA digestion, 800 ul of isopropyl alcohol was added to the mixture and the mixture was left at room temperature for 5 minutes. The mixture was then centrifuged at 15,000 rpm for 15 minutes at 4° C. and the pellet was rinsed with 70% ethanol, dried and resuspended in 50 ul of TE. The chromosomal DNA thus recovered was used in the following step.

Screening of Chromosomal DNA Using an Oligomer Having Part of the neo Gene Sequence The foreign DNA incorporated in the chromosome was specifically amplified by a polymerase chain reaction method (PCR: Saiki, R. K., et.al., 1986, Nature 324:163–166). The amplified foreign DNA was electrophoresed on agarose gel and the DNA band on the gel was transferred to a nylon filter. The presence of the foreign DNA was detected using part of a neo gene as a probe. Specifically, two primers were synthesized by DNA synthesizer (Applied Biosystem; 380A); 10 complementary primers 5'-AACA AGATGGATTGCACGCA-3'(neo-1) SEQ ID NO. 1, corresponding to the sequence near the ATG codon (nucleotide number 1558 to 1577 on a neo gene) and another complementary primer 5'-CTTGACAA AAAGAACCGGC- 3' (neo-2) (SEQ ID NO. 2) corresponding to the sequence about 130 bp downstream of ATG codon of the neo gene (nucleotide number 1681 to 1700) were synthesized. The foreign DNA contained the neo gene (derived from Tn described in Beck, E., et. al., 1982,Gene., 9; 327–336 ), which confers cells resistance against G-418, an analogue of neomycin. 4.9 ul of chromosomal DNA (2 ng), 1 ul of neo-1 (10 pM), 1 ul of neo-2 (10 pM), 2 ul of dNTPs (200 uM), 0.1 ul of Ampli Taq™ polymerase (0.5 U; TAKARA No. 2531 ), and 1 ul of PCR buffer (10×) were combined in a microfuge tube (Sarstedt; No. 72. 699). 20 ul of paraffin oil (Sigma; No. 400–5) was placed on the top of the mixture and PCR was carried out using DNA thermal cycler (Abe Science; Tomcom 2). The template chromosomal DNA was denatured at 95° C., and 40 cycles were performed with a temperature of 95° C. for a minute, 56° C. for 2 minutes, and 72° C. for 2 minutes. After the PCR, the mixture was removed and 10 ul of the mixture was electrophoresed on a 2% agarose gel. The gel was then immersed in a solution containing 0.5N NaOH and 1.5M NaCl for 30 minutes. The DNA on the gel was blotted onto a nylon filter using 20× SSC (3M NaCl, 0.3M sodium citrate). The filter was then baked at 80° C. for 2 hours. The Southern hybridization was carried out using a DNA probe, about 1 kb BglII (at nucleotide 1515 )-SmaI (at nucleotide 2516) segment of the neo gone. The chromosomal DNA was screened for the presence of the incorporated foreign DNA. If the 142bp segment between primer neo-1 and neo-2 was present in the chromosomal DNA, a hybridization signal should be detected. In case the segment was absent, no hybridization signal would be found.

EXAMPLE 1

2–7.5×10$^5$ cells of CHO-dhfr$^-$ (dihydrofolate reductase deficient cell line; Urlaub, G., and Chasin, L. A., 1980, Proc. Natl. Acad. Sci. U.S.A., 77; 4216–4422) were plated in a 60 mm plate (Falcon; No. 3002) containing 4 ml of MEM-α$^+$ (Gibco)+10% fetal calf serum the day before the addition of one compound: DNA complex. The plate was incubated at 37° C., under 5%CO$_2$/95% air atmosphere. The following day the culture medium was replaced with a medium containing the Ho 33342: DNA complex. The culture medium containing the Ho 33342:DNA complex was prepared just before adding the medium to cells: a proper concentration of the DNA (a foreign DNA) in TE and a proper concentration of the Ho 33342 stock solution (500 ug of Ho 33342 was dissolved in 1 ml of distilled water and the solution was stored in dark at 4° C.) were combined. Distilled water was added to the mixture to bring the volume to 100 ul. The mixture was gently swirled and then placed in dark at room temperature for more than 10 minutes. The foreign DNA was pSV2neo (Gorman, C., et.al., 1983, Science., 221; 551–553). 100 ul of the Ho 33342: DNA complex was then added to 4 ml of MEM-α$^+$+10% fetal calf serum and cultured for 20 hours.

The medium containing the complex was discarded and the cells were rinsed 3× with serum-free MEM-α$^+$. 4 ml of a culture medium containing a fresh MEM-α$^+$ and 10% fetal calf serum was added to the cells and the culture was incubated for 46 hours. The cells were trypsinized and the cell number was counted. 5×10$^4$ cells were plated in a 100 mm plate (Falcon; No.3003) containing 7 ml of a culture medium [400 ug/ml of G-418 (Gibco; No. 860–1811), MEM-α$^+$, 10% fetal calf serum]. The culture was incubated for 12 days with a change of the medium every three days. Table 1 shows the number of G-418 resistant colonies per plate on day 14.

TABLE 1

| Plasmid DNA (ug) | Ho 33342 (uM) | Number of colonies on day 14 |
| --- | --- | --- |
| 1 | 0 | 0 |
| 1 | 2 | 0 |
| 1 | 6 | 2 |
| 1 | 12.5 | 3 |

It is evident from Table 1 that G-418 resistant colonies were found in the plates treated with the Ho 33342: foreign DNA complex. The plates treated with the DNA alone did not produce a G-418 resistant colony at all, even starting with a higher cell density (e.g., 5×10$^5$ or 5×10$^6$).

G-418 non-resistant cells were transformed into a G-418 resistant cells, suggesting that the foreign DNA was incorporated in the chromosomal DNA of the G-418 non-resistant cells and the G-418 resistant gene was expressed in the cells. The incorporation of the foreign DNA in the transformed cells was continued as follows: the cell was removed from the plate by aspiration under the microscope and grown further to obtain the DNA. The chromosomal DNA was isolated from the cell, amplified by the PCR, and electrophoresed on the gel. A 142 bp band, the size of the foreign DNA, was found in the lane of the transformed cell, but not in the lane of the control (cells not transfected) (FIG. 1).

EXAMPLE 2

The CHO-dhfr$^-$ cell was grown as described in Example 1 except that the culture medium used was free of fetal calf serum. Table 2 shows the number of the G-418 resistant colonies on day 14 after treatment with the Ho 33342: DNA complex.

TABLE 2

| Plasmid DNA (ug) | Ho 33342 (uM) | Number of colonies on day 14 |
| --- | --- | --- |
| 1 | 0 | 0 |
| 1 | 2 | 1 |
| 1 | 6 | 1 |
| 1 | 12.5 | 18 |

12.5 uM Ho 33342, a relatively high concentration of the compound, in combination with the serum-free culture medium has remarkably increased transformation efficiency.
Effect of the Invention According to this invention, foreign DNA can be introduced into a host cell easily and efficiently.

What is claimed is:

1. A method of introducing a foreign DNA into a chromosome of a mammalian cell comprising exposing said cell, in a suspension or a solution, to a complex comprising foreign DNA and a carrier, wherein said carrier is selected from the group consisting of 2-[2-(4-hydroxyphenyl)benzimidazolyl-5]-5-(4 -methylpiperazinyl-1) -benzimidazole and 2-[2-(4-ethoxyphenyl)benzimidazolyl-5]-5-(4-methylpiperazinyl)-benzimidazole.

2. A method according to claim 1 that utilizes a conventional transformation method.

3. A method according to claim 1 wherein said foreign DNA is inserted into PSVneo.

4. A transformed mammalian cell obtained from a method according to claim 1,2 or 3.

5. A mammalian cell of claim 4, characterized in that said cell is a rodent cell.

6. A mammalian cell of claim 4, characterized in that said cell is a sperm cell or egg cell.

* * * * *

UNITED STATES PATENT AND TRADEMARK OFFICE
CERTIFICATE OF CORRECTION

PATENT NO. : 5,595,899
DATED : January 21, 1997
INVENTOR(S) : Masahiro SATO et al.

It is certified that error appears in the above-indentified patent and that said Letters Patent is hereby corrected as shown below:

Claim 3, column 10, line 35, "PSVneo" should read --pSVneo--.

Signed and Sealed this

Twenty-fourth Day of June, 1997

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

AACAAGATGG ATTGCACGCA 20

( 2 ) INFORMATION FOR SEQ ID NO:2:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CTTGACAAAA AGAACCGGC 19